United States Patent [19]

Cameto et al.

[11] 4,181,129

[45] Jan. 1, 1980

[54] INFANT HOOD

[75] Inventors: Leon R. Cameto, Oakland; John R. Edmund, Berkeley, both of Calif.

[73] Assignee: MistO$_2$Gen Equipment Company, Oakland, Calif.

[21] Appl. No.: 871,887

[22] Filed: Jan. 25, 1978

[51] Int. Cl.[2] .......... A61M 16/02

[52] U.S. Cl. .......... 128/205.26

[58] Field of Search .......... 128/205, 172, 185, 186, 128/191 A, 192, 195, 201, 203, 204, 205, 141 R, 142.7, 1 B, 30.2

[56] References Cited

U.S. PATENT DOCUMENTS

| | | | |
|---|---|---|---|
| 2,508,050 | 5/1950 | Valente | 128/205 |
| 2,764,152 | 9/1956 | Osterberg | 128/205 X |
| 3,710,791 | 1/1973 | Deaton | 128/191 A |
| 4,022,200 | 5/1977 | Jonson | 128/204 X |

FOREIGN PATENT DOCUMENTS

| | | | |
|---|---|---|---|
| 219851 | 3/1910 | Fed. Rep. of Germany | 128/185 |

*Primary Examiner*—Henry J. Recla

*Attorney, Agent, or Firm*—Townsend and Townsend

[57] ABSTRACT

An improved infant hood of the type having a wall portion with an opening surrounding the infant's neck and a cover member for fitting on top of the wall. The wall portion comprises a flat but flexible rectangular sheet having holes at the opposite ends. The sheet is flexed into a generally cylindrical shape and the opposite ends are secured to one another by flexible rivets which pass through the holes, thus forming the cylindrical wall. When not in use the cover member and flat sheet are retained to one another by the same rivets which secure the opposite ends of the sheet to one another.

7 Claims, 4 Drawing Figures

INFANT HOOD

BACKGROUND OF THE INVENTION

The present invention relates to a hood or tent for providing a controlled environment for infants. More specifically, the invention relates to an improvement which permits the infant hood to be disassembled into a flat configuration for ease of cleaning and storage.

A hood capable of covering an infant's head while the infant is lying in a crib or incubator is often used to provide a controlled environment for administering high concentrations of oxygen, humidity, or antibiotics in the form of aerosols. The typical infant hood comprises an enclosed wall, usually of cylindrical shape, made of transparent material and having a cutout for the infant's head, and a transparent cover member which fits over the wall. The oxygen, water vapor mist, or aerosol passes into the hood through an opening in the wall. Openings are also provided in the wall for the insertion of intravenous tubes. The cover of the hood has openings for monitoring temperature and oxygen concentration. The cutout or opening in the wall which fits over the infant's neck is sufficiently large to provide space for preventing the accumulation of carbon dioxide gas.

Typical infant hoods are inherently bulky. Thus, they are difficult to store and clean. Because there is no way to secure the two portions of the hood to one another when the hood is not in use, the walls and covers are often misplaced. Furthermore, a situation often arises where, because of a special need of a particular infant, additional holes must be cut into the infant hood. The fixed cylindrical wall of present hoods makes the cutting of additional holes extremely difficult.

Accordingly, the primary object of the present invention is to provide a collapsible infant hood which can be easily cleaned and stored in a flat configuration and in which the two major portions of the hood can be secured to one another when the hood is not in use. A further object of the invention is to permit easy cutting of additional holes in the walls when required.

SUMMARY OF THE INVENTION

The present invention solves the problems associated with typical infant hoods. The invention is directed to a collapsible hood comprising generally two main elements. A rectangular sheet, having a normally flat configuration, is flexed into a cylindrical shape and the ends of the sheet are secured to one another to retain the cylindrical shape, thus forming a cylindrical wall. A cover member fits over the cylindrical wall. When not in use, the hood is disassembled by removing the cover and disconnecting the ends of the sheet, permitting the sheet to return to its generally flat shape. Thus, in a flat configuration, the two portions of the hood can be readily cleaned. Flexible rivets which retain the ends of the sheet to one another when the hood is constructed are used to secure the cover to the sheet when the hood is disassembled. Because the cover and sheet have a generally flat shape when not in use, the collapsed hood takes up very little space and can be readily stored. Further, the retention of the cover member and the flat sheet to one another during non-use prevents misplacing one of the portions of the hood.

The novel features which are believed to be characteristic of the invention, together with further objects and advantages thereof, will be better understood from the following description considered in connection with the accompanying drawings in which preferred embodiments of the invention are illustrated by way of example. It is to be expressly understood, however, that the drawings are for the purpose of illustration and description only and are not intended as a definition of the limits of the invention.

DESCRIPTION OF THE PREFERRED EMBODIMENT

Figure 2:
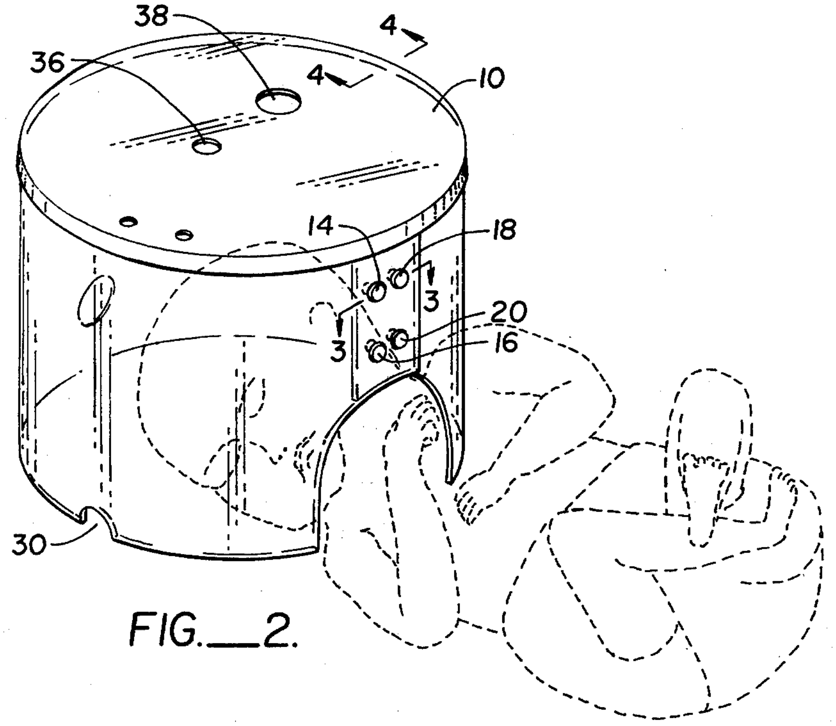
FIG. 2 is an illustration of the hood in use.
Figure 1:
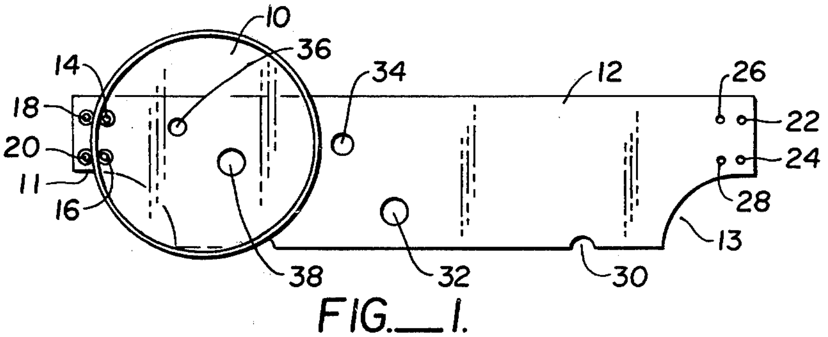
FIG. 1 is an illustration of the two major portions of the hood in the collapsed state.

The infant hood comprises two main parts, a cover plate 10 and a rectangular sheet 12, as shown in FIG. 1. When not in use, the two parts are secured to one another by flexible rivets 14 and 16, so as to prevent accidental misplacement of either the cover plate or the sheet. The flat arrangement of the two parts permits easy cleaning, such as by washing in a detergent, and easy storage of the hood when not in use. Further, the flat arrangement allows easy insertion of the disassembled hood into a gas or steam autoclave for sterilization.

The flat sheet 12 is of a transparent material, such as a polyvinyl or polycarbonate. At opposite corners along the lower lengthwise edge of the sheet are quarter-circular shaped notches 11 and 13, respectively. On each end of the sheet is a plurality of holes, such as holes 22, 24, 26 and 28. Holes 32 and 34 permit the insertion of one or more hoses to supply oxygen, water vapor or aerosols into the hood. A notch 30 on the lower lengthwise edge of the sheet permits an intravenous or other type tube to be inserted under the hood. The cover plate 10 also has openings 36 and 38 for the insertion of temperature and oxygen concentration probes to monitor the environment within the hood.

Figure 4:
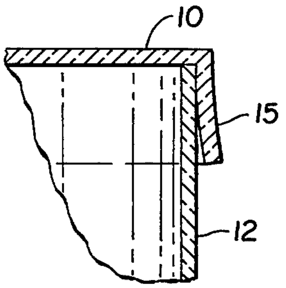
FIG. 4 is a sectional view illustrating the cover plate fitted over the cylindrical wall.

The hood is constructed by first removing the cover plate from the rectangular sheet by bending the flexible rivets 14 and 16 as will be more fully discussed below. The rectangular sheet, being of a thin, flexible material such as polycarbonate, is then flexed into a generally cylindrical shape. The respective holes on the opposite ends of the sheet are aligned with one another and the four rivets are inserted through the holes to connect the sheet and retain it in a cylindrical shape so as to form the cylindrical wall portion of the infant hood. As shown in FIG. 4, the cover member is then secured over the cylindrical wall and further aids in securing the ends of the sheet to one another and in generally conforming the shape of the wall to a cylinder. The cover has a downwardly extending flange 15 around its periphery. The flange is outwardly flared, as shown in FIG. 4, to permit easy insertion over the cylindrical wall. The inner diameter of the peripheral flange is sufficient to fit securely over the cylindrical wall, thus forming a relatively tight seal.

While in the preferred embodiment, flexible rivets secure the ends of the sheet to one another, other suitable means may accomplish the same result. For example, if the flange provides a tight enough seal with the cylindrical wall, it will suffice to retain the flexible sheet in its cylindrical shape.

Figure 3:
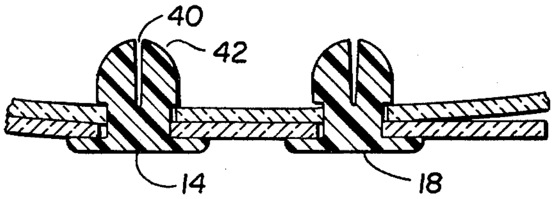
FIG. 3 is a sectional view through the rivets retaining the ends of the sheet.

A more detailed view of the flexible rivets is shown in FIG. 3. The rivets are generally of a plastic material and have slots, such as the slot 40 on rivet 14. The slot permits the two portions of the rivet nose 42 to be flexed together to withdraw the rivet when the hood is to be collapsed. The snub nose 42 of the rivet permits easy insertion of the rivet into a hole. The two portions of the nose are forced together closing the slot when the rivet is first inserted into the hole. Once the rivet has passed completely through the hole, the two portions return to their relaxed shape as shown in FIG. 3.

It will be noted that this invention involves a substantial improvement in the typical infant hood. The hood can be disassembled into its two general components and placed in a flat configuration for easy cleaning and storage. The two components are retained to one another by the same rivets which secure the opposite ends of the rectangular sheet to one another, thus preventing misplacement of one of the components. Further, the flexible sheet permits easy cutting of additional holes in the walls, such as by punching or drilling the sheet when it is in a flat configuration.

While the preferred embodiment of the present invention has been illustrated in detail, it is apparent that modifications and adaptations of that embodiment will occur to those skilled in the art. However, it is to be expressely understood that such modifications and adaptations are within the sphere and scope of the present invention.

I claim:

1. An improved hood for covering an infant's head and providing a generally controlled environment, said hood being of the type having a cover plate and side walls having an opening for the infant's head and at least one other opening for the introduction of a gas, wherein the improvement comprises:

- a generally flat sheet, said sheet being flexible so as to contact opposite ends of said sheet with one another, thereby forming generally cylindrically configured side walls;
- a generally circularly shaped cover plate having a flange extending from the peripheral edge, said flange having an internal diameter sufficiently exceeding that of the cylindrically configured side walls so as to provide a substantially tight fit therewith; and
- means for releasably securing said opposite ends of said sheet to one another so as to maintain said side walls in a generally cylindrical configuration.

2. Apparatus according to claim 1 wherein said opposite ends of said sheet have holes and wherein said securing means further comprises flexible rivets for insertion into said holes.

3. Apparatus according to claim 1 wherein said sheet and said cover plate are polycarbonate.

4. Apparatus according to claim 1 including means for connecting said cover plate to said sheet when said sheet has a generally planar shape.

5. Apparatus according to claim 1 wherein said opposite ends of said sheet have notches defining an opening for the infant's head when said opposite ends are secured to one another.

6. Apparatus according to claim 5 wherein said notches are located on the corners of said sheet.

7. An improved infant hood of the type having a circular shaped cover plate and a cylindrical wall with openings in the wall for the infant's head, an intravenous tube, and a gas supply hose, wherein the improvement comprises:

- a generally flat sheet having a generally rectangular shape, said sheet being flexible about an axis generally parallel to its width so as to form the cylindrical wall of the hood, said sheet having at least one generally semicircular shaped notch on the first lengthwise edge for the insertion of an intraveneous tube, generally quarter-circular shaped notches at the opposite ends of said first lengthwise edge defining an opening for the infant's head when said sheet is flexed to form the cylindrical wall, an opening for the insertion of a gas supply hose, and holes proximate each of two widthwise edges;
- a plurality of flexible rivets insertable through the holes on said sheet for releasably securing the width-wise ends of said sheet to one another so as to maintain the wall of the hood in a generally cylindrical shape; and
- a circularly shaped cover plate for overlapping engagement with the second lengthwise edge of said sheet flexed to form the cylindrical wall, said plate having holes of substantially the same size as the holes on said sheet for the insertion of said rivets to releasably secure said cover plate to said sheet when said sheet has a generally flat shape.

* * * * *